United States Patent
Zotkin et al.

(10) Patent No.: US 10,442,758 B2
(45) Date of Patent: Oct. 15, 2019

(54) ZINC OR COPPER (II) SALT AND USE THEREOF AS A BIOCIDE

(71) Applicant: LABORATORIYA BIO ZET, LLC, Nizhny Novgorod (RU)

(72) Inventors: Igor I. Zotkin, Nizhny Novgorod (RU); Nadezhda V. Kuznetsova, Nizhny Novgorod (RU); Larisa V. Kabanova, Nizhny Novgorod (RU)

(73) Assignee: LABORATORIYA BIO ZET, LLC, Moscow (RU)

( * ) Notice: Subject to any disclaimer, the term of this patent is extended or adjusted under 35 U.S.C. 154(b) by 53 days.

(21) Appl. No.: 15/088,588

(22) Filed: Apr. 1, 2016

(65) Prior Publication Data

US 2016/0214931 A1 Jul. 28, 2016

Related U.S. Application Data

(63) Continuation of application No. PCT/RU2013/000884, filed on Oct. 8, 2013.

(51) Int. Cl.
| | |
|---|---|
| C07C 309/63 | (2006.01) |
| C07C 65/05 | (2006.01) |
| A01N 37/10 | (2006.01) |
| A01N 41/04 | (2006.01) |
| C07C 63/08 | (2006.01) |
| C09D 5/14 | (2006.01) |
| D21H 21/36 | (2006.01) |
| C07F 1/00 | (2006.01) |
| C07F 3/00 | (2006.01) |
| C08K 5/00 | (2006.01) |
| C08K 5/098 | (2006.01) |
| A01N 37/06 | (2006.01) |
| B27K 3/38 | (2006.01) |

(52) U.S. Cl.
CPC ............ *C07C 309/63* (2013.01); *A01N 37/06* (2013.01); *A01N 37/10* (2013.01); *A01N 41/04* (2013.01); *C07C 63/08* (2013.01); *C07C 65/05* (2013.01); *C07F 1/005* (2013.01); *C07F 3/003* (2013.01); *C08K 5/0058* (2013.01); *C08K 5/098* (2013.01); *C09D 5/14* (2013.01); *D21H 21/36* (2013.01); *B27K 3/38* (2013.01)

(58) Field of Classification Search
CPC .................................................... C07C 49/794
USPC ........................................................ 568/335
See application file for complete search history.

(56) References Cited

U.S. PATENT DOCUMENTS

| | | | |
|---|---|---|---|
| 4,258,090 A | 3/1981 | Moraru | |
| 4,670,492 A * | 6/1987 | Nakahara | ............ C07F 9/65744 524/119 |
| 5,185,033 A | 2/1993 | Hani et al. | |
| 5,298,061 A | 3/1994 | Waldron et al. | |
| 5,460,644 A | 10/1995 | Thomassen | |
| 5,540,954 A | 7/1996 | Nicholas et al. | |
| 5,717,007 A | 2/1998 | Cambon | |
| 6,399,560 B1 | 6/2002 | Kwon et al. | |
| 6,858,658 B2 | 2/2005 | Tomasgaard et al. | |
| 7,410,553 B2 | 8/2008 | Blanpied et al. | |
| 2008/0219944 A1 | 9/2008 | Longo et al. | |
| 2009/0223408 A1 | 9/2009 | Richardson et al. | |

FOREIGN PATENT DOCUMENTS

| | | |
|---|---|---|
| CN | 1511909 A | 7/2004 |
| CN | 102167775 A | 8/2011 |
| EP | 2161316 A1 | 3/2010 |
| EP | 2360214 A1 | 8/2011 |
| JP | 48040909 * | 12/1973 |
| RU | 95102413 A1 | 3/1997 |
| RU | 2111993 C1 | 5/1998 |
| RU | 2162870 C2 | 2/2001 |
| RU | 2169163 C1 | 6/2001 |
| RU | 2278515 C2 | 6/2006 |
| RU | 2315793 C1 | 1/2008 |
| RU | 2318942 C1 | 3/2008 |
| RU | 2377121 C2 | 12/2009 |
| RU | 2378363 C1 | 1/2010 |
| RU | 2395548 C1 | 7/2010 |
| RU | 2398804 C2 | 9/2010 |
| RU | 2415168 C2 | 3/2011 |
| RU | 2497857 C1 | 11/2013 |

OTHER PUBLICATIONS

International Search Report from International Application No. PCT/RU2013/000884, filed Oct. 8, 2013, dated Jul. 16, 2014.

* cited by examiner

*Primary Examiner* — Leslie A. Royds Draper
*Assistant Examiner* — William Y Lee
(74) *Attorney, Agent, or Firm* — Patentbar International, PC

(57) ABSTRACT

There is provided as a biocide zinc or copper (II) salt having the general formula $CH_2=C(R^1)COO-M-OCOC_6H_3R^2R^4$, wherein M is Zn or Cu, $R^1$ is selected from the group comprising hydrogen and methyl, $R^2$ is selected from the group comprising hydrogen and OH, $R^4$ is selected from the group comprising hydrogen, alkyl and $SO_2OH$ group.

3 Claims, No Drawings

ZINC OR COPPER (II) SALT AND USE THEREOF AS A BIOCIDE

RELATED APPLICATIONS

This Application is a Continuation application of International Application PCT/RU2013/000884, filed on Oct. 8, 2013, which is incorporated herein by reference in its entirety.

FIELD OF THE INVENTION

The invention relates to new chemical compounds—zinc and copper salts with organic acids, which can find application as biocides.

BACKGROUND OF THE INVENTION

Various zinc and copper compounds exhibiting biocidal activity are known in the art, in particular, zinc and copper oxides and inorganic salts (RU 95102413, C09D 5/14, 1997; RU 2162870, C09D 5/02, C09D 5/14, 2001; RU 2395548, C09D 5/14, B82B 1/00, 2010; RU 2398804, C09D 5/14, A01N 59/00, A01N 47/00, B82B 1/00, 2010; U.S. Pat. No. 5,540,954, A01N 59/16, A01N 59/20, B27K 3/52, B05D 07/06, A01N 31/08, A01N 31/00, 1996; U.S. Pat. No. 6,858,658, A01N 59/20, A01N 59/16, C09D 5/16, C08K 03/10, C08K 03/18, C08K 03/22, 2005; US 20080219944, C09D 5/16, 2008; US 20090223408, C09D 5/16, C09D 5/14, 2009), zinc and copper naphthenates or resinates (RU 2377121, B27K 3/50, B27K 3/52, B27K 3/22, 2009; EP 2161316, C09D 133/06, C09D 133/12, C09D 143/04, C09D 5/16, C09D 7/12, 2010; EP 2360214, C09D 143/04, C09D 193/04, C09D 5/16, 2011; U.S. Pat. No. 4,258,090, C04B 41/45, C04B 41/52, C04B 41/60, C04B 41/70, B05D 03/02, 1981), ammonia complexes of zinc salts (U.S. Pat. No. 5,460,644, C08K 3/10, C08K 3/00, C09D 5/14, C09D 5/00, 1995), zinc and copper pyrithionates (bis-(2-pyridylthio)-1, 1'-dioxides) (RU 2111993, C09D 5/14, C09D 5/16, 1998; RU 2415168, C09D5/16, C09D5/14, 2011; U.S. Pat. No. 5,185,033, C09D 5/14, C09D 5/16, 1993; U.S. Pat. No. 5,298,061, C09D 5/16, C09D 5/14, 1994; U.S. Pat. No. 5,717,007, C09D 5/16, C08L, 33/10, C08K 05/17, C08K 05/18, 1998; U.S. Pat. No. 6,399,560, A01N 43/40, A01N 43/34, A61L 2/18, C11D 3/48, 2002; U.S. Pat. No. 7,410,553, D21C 5/02, B32B 27/04, D21G 1/02, 2008). The above mentioned compounds were used with various degrees of efficiency as additives to coatings intended for treatment of building structures, prevention of underwater structures and ship parts from fouling as well as for paper and wood treatment.

The closest analogue of the proposed compounds is zinc salt with acetic and methacrylic acids, i.e. zinc methacrylate-acetate (hereinafter referred to as ZMA) exhibiting a certain biocidal activity when compounded with aqueous styrene-acrylic dispersion being used as polymer primer for applying paint coatings to various surfaces (RU 2315793, C09D 5/14, C09D 131/02, C09D 133/10, 2008).

SUMMARY OF THE INVENTION

To provide new means effecting on various biological substrates, there is proposed zinc or copper (II) salt having the general formula:

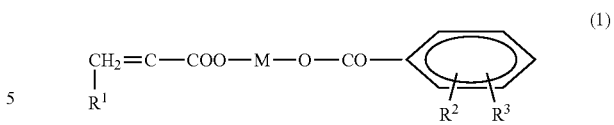

wherein M is Zn or Cu,
$R^1$ is selected from the group comprising hydrogen and methyl,
$R^2$ is selected from the group comprising hydrogen and OH,
$R^3$ is selected from the group comprising alkyl and $SO_2OH$ group.

To solve the same problem it is proposed to use as a biocide zinc or copper 11 salt having the general formula:

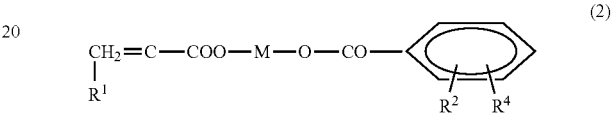

wherein M is Zn or Cu,
$R^1$ is selected from the group comprising hydrogen and methyl,
$R^2$ is selected from the group comprising hydrogen and OH,
$R^4$ is selected from the group comprising hydrogen, alkyl and $SO_2OH$ group. It was surprisingly found that zinc and copper (II) salts corresponding to formula (2) which covers new compounds of formula (1), as well as formerly known zinc acrylate-benzoate and copper methacrylate-benzoate (CN 102167775, 2011), the biocidal activity of which has not been known before, have much higher biocidal activity than ZMA and, besides, wide spectrum of effect on biological matters. Thus, they can be used not only in coating compositions but also in disinfectant compositions of various purpose, paper and wood treatment compositions, polymer compositions with higher fungus resistance as well as in many methods preventing organisms and materials from adverse effect of biological matters.

DETAILED DESCRIPTION OF THE PREFERRED EMBODIMENTS

The essence of the invention is illustrated by examples given below. Examples 1-8 describe the preparation and properties of certain representatives of the proposed series of substances, examples 9-23—their bactericidal and fungicidal activity.

Example 1

10 g of sulfosalicylic acid, 100 ml of distilled water are placed into a 500 ml round-bottom flask and the solution is stirred until sulfosalicylic acid is completely dissolved. Then a suspension of 3.64 g of zinc oxide in 50 ml of distilled water is gradually added to the solution under constant stirring and whereupon 3.2 g of acrylic acid is added and stirred until the suspension is completely dissolved. The obtained solution is evaporated to dryness at a temperature of not more than 70° C., and the resulted solid product is subjected to recrystallization from distilled water, 12.1 g of water-soluble powdered zinc acrylate-sulfosalicylate is obtained which corresponds to the above general formula wherein $R^1$=H, $R^2$=$SO_2OH$, $R^3$=OH (79% yield of the stoichiometric). The results of elemental analysis of salts obtained as described in this and subsequent examples are given in Table 1.

Example 2

Zinc methacrylate-benzoate ($R^1$=$CH_3$, $R^2$=H, $R^3$=H) with melting point of 283° C. is obtained in 68% yield of the stoichiometric by analogy with Example 1 using benzoic and methacrylic acids instead of sulfosalicylic and acrylic ones (respectively).

Example 3

Zinc methacrylate-salicylate ($R^1$=$CH_3$, $R^2$=OH) with melting point of 250° C. is obtained in 80% yield of the stoichiometric by analogy with Example 1 using salicylic and methacrylic acids instead of sulfosalicylic and acrylic ones (respectively).

Example 4

Zinc methacrylate-sulfosalicylate ($R^1$=$CH_3$, $R^2$=$SO_2OH$, $R^3$=OH) with melting point of 238° C. is obtained in 82% yield of the stoichiometric by analogy with Example 1 using methacrylic acid instead of acrylic one.

Example 5

Zinc methacrylate-toluylate ($R^1$=$CH_3$, $R^2$=$CH_3$, $R^3$=H) is obtained in 80% yield of the stoichiometric by analogy with Example 1 using toluylic and methacrylic acids instead of sulfosalicylic and acrylic ones respectively).

Example 6

Zinc acrylate-benzoate ($R^1$=H, $R^2$=H, $R^3$=H) with melting point of 238° C. is obtained in 55% yield of the stoichiometric by analogy with Example 1 using benzoic acid instead of sulfosalicylic one. The structure of the obtained individual compound is verified by NMR spectra analysis, in NMR spectrum $^1H$, multiplets in the regions 5.62÷5.72 and 6.15÷6.30 ppm belong to protons of $H_2C$=CH—C(O)O acrylate group. Benzoic group displays signals at $\delta_H$ 7.38 (triplet), 7.48 (triplet) and 8.06 ppm (doublet). In NMR spectrum $^{13}C$, benzoic group displays signals at $\delta_C$ 129.0 (m-CH), 131.0 (o-CH), 132.8 (p-CH), 135.2 ($C_1$), 175.4 ppm (OC(=O)), and acrylate group displays signals at $\delta_C$ 129.0 and 133.2 ($H_2C$=CH—), 175.1 ppm (OC(=O)).

Example 7

Copper acrylate-benzoate ($R^1$=H, $R^2$=H, $R^3$=H) is obtained in 55% yield of the stoichiometric by analogy with Example 1 using benzoic acid instead of sulfosalicylic one and copper oxide instead of zinc oxide.

Example 8

Copper methacrylate-salicylate ($R^1$=$CH_3$, $R^2$=H, $R^3$=OH) is obtained in 85% yield of the stoichiometric by analogy with Example 1 using salicylic and methacrylic acids instead of sulfosalicylic and acrylic ones (respectively) and copper oxide instead of zinc oxide.

Example 9

Bactericidal activity of zinc methacrylate-salicylate obtained as described in Example 3 and zinc methacrylate-sulfosalicylate obtained as described in Example 4 is determined according to the known method (RU 2378363, C12N 1/00, C12Q 1/00, 2010) based on the exposure of a bacterial culture in a solution of bactericidal substance for a certain period of time followed by its neutralization and inoculation of the culture on a solid nutrient medium. The sensitivity of microorganisms to a disinfectant is judged by microorganism growth on the nutrient medium up to 300 CFU/ml (CFU—colony-forming unit): in particular, growth up to 100 CFU/ml exhibits incomplete bactericidal effect, growth up to 100-300 CFU/ml—sub-bactericidal effect and growth up to more than 300 CFU/ml exhibits resistance of microorganisms to a disinfectant. The determination is performed on *E. coli* No. 906 and *S. aureus* No. 1257 test strains being usually used to study the bactericidal activity of biocides as well as on clinical strains—*P. aeruginosa* and methicillin-resistant strain *S. aureus*—at salt concentrations from 0.5 to 2% and time of exposure from 5 to 60 min. Test results are given in Table 2. It follows from Table 2 that zinc methacrylate-salicylate at concentration of 1.0% exhibits stable bactericidal effect against all strains at time of exposure from 30 min. At concentration of 2.0%, it exhibits the same bactericidal effect at time of exposure from 5 min. Zinc methacrylate-sulfosalicylate at concentration of 1.0% also exhibits stable bactericidal effect against three of four investigated strains at time of exposure from 30 min.

Example 10 (Comparative)

The same method as described in Example 9 is used to determine the bactericidal activity of ZMA against three of four strains studied in Example 9. Test results are given in Table 3. From Table 3 it follows that the bactericidal activity of ZMA is substantially lower than that of the proposed salts: it exhibits stable bactericidal activity against *E. coli* No. 906 at time of exposure of 30 min. and concentration from 1.0 to 2.5%, not completely stable bactericidal activity against *P. aeruginosa*—only at concentration from 2.5%, and sub-bactericidal activity against *S. aureus* No. 1257—only at concentration of 2.5% and time of exposure of 60 min.

Examples 11-23

The fungicidal activity of the proposed salts is determined according to GOST 30028.4-2006 by testing samples of various materials treated with these salts for resistance to fungal spores. Test results in terms of tolerance time (in days) are given in Table 4 wherein tolerance time for untreated and ZMA-treated materials are given for comparison. It follows from Table 4 that the fungicidal activity of the proposed salts exceeds the fungicidal activity of ZMA.

INDUSTRIAL APPLICABILITY

The present invention can be used for production of biocides intended, for example, for incorporation into polymer materials, disinfectant and antiseptic compositions, treatment of wood, paper, building structures and other materials to prevent their damage caused by biological matters (microorganisms, fungi, algae), manufacture of various articles with biocidal properties, etc.

TABLE 1

Results of elemental analysis of salts

| Example | Name | Empirical formula | Sample weight, g | C, g calculated | C, g determined | H, g calculated | H, g determined | Zn, g calculated | Zn, g determined | Cu, g calculated | Cu, g determined | S, g calculated | S, g determined |
|---|---|---|---|---|---|---|---|---|---|---|---|---|---|
| 1 | Zinc acrylate-sulfo-salicylate | $C_{10}H_8O_8SZn$ | 0.5 | 0.170 | 0.165 | 0.011 | 0.012 | 0.093 | 0.093 | | | 0.045 | 0.044 |
| 2 | Zinc methacrylate-benzoate | $C_{11}H_{10}O_4Zn$ | 0.5 | 0.242 | 0.25 / 0.24 | 0.020 | 0.019 / 0.021 | 0.120 | 0.120 / 0.117 | | | | |
| 3 | Zinc methacrylate-salicylate | $C_{11}H_{10}O_5Zn$ | 0.5 | 0.230 | 0.20 / 0.21 | 0.0175 | 0.016 / 0.014 | 0.114 | 0.100 / 0.091 | | | | |
| 4 | Zinc methacrylate-sulfo-salicylate | $C_{11}H_{10}O_8SZn$ | 0.5 | 0.180 | 0.182 / 0.178 | 0.0137 | 0.013 / 0.0135 | 0.089 | 0.08 / 0.087 | | | 0.045 | 0.042 |
| 5 | Zinc methacrylate-toluylate | $C_{12}H_{12}O_4Zn$ | 0.5 | 0.252 | 0.25 / 0.265 | 0.021 | 0.015 / 0.0165 | 0.114 | 0.11 / 0.116 | | | | |
| 6 | Zinc acrylate-benzoate | $C_{10}H_8O_4Zn$ | 0.5 | 0.233 | 0.24 / 0.238 | 0.0156 | 0.015 / 0.0165 | 0.127 | 0.12 / 0.126 | | | | |
| 7 | Copper acrylate-benzoate | $C_{10}H_8O_4Cu$ | 0.5 | 0.235 | 0.24 / 0.235 | 0.0158 | 0.0156 / 0.016 | | | 0.124 | 0.125 / 0.128 | | |
| 8 | Copper methacrylate-salicylate | $C_{11}H_{10}O_5Cu$ | 0.5 | 0.231 | 0.21 / 0.205 | 0.0176 | 0.0155 / 0.016 | | | 0.111 | 0.115 / 0.1 | | |

TABLE 2

Bactericidal activity of zinc methacrylate-salicylate and zink methacrylate-sulfosalicylate

| Concentration, % wt. | Time of exposure, min. | Zinc methacrylate-salicylate | | | | Zinc methacrylate-sulfosalicylate | | | |
|---|---|---|---|---|---|---|---|---|---|
| | | E. coli 1257 | S. aureus 906 | P. aeruginosa | S. aureus | E. coli 906 | S. aureus 1257 | P. aeruginosa | S. aureus |
| 2.0 | 30 | NG | NG | NG | NG | | | | |
| | | NG | NG | NG | NG | | | | |
| | | NG | NG | NG | | | | | |
| | | NG | NG | NG | | | | | |
| | | NG | NG | NG | | | | | |
| | 15 | NG | NG | NG | NG | | | | |
| | | NG | NG | NG | NG | | | | |
| | 5 | NG | NG | NG | NG | | | | |
| | | NG | NG | NG | NG | | | | |
| 1.0 | 60 | NG | NG | NG | NG | NG | NG | NG | 101 CFU |
| | | NG | NG | NG | | NG | NG | NG | 30 CFU |
| | | | | | | NG | NG | NG | |
| | | | | | | NG | NG | NG | |
| | 30 | NG | NG | NG | NG | NG | NG | NG | |
| | | NG | NG | NG | | NG | NG | NG | |
| | | | | | | NG | >300 CFU | NG | |
| | 15 | NG | NG | NG | 40 CFU | NG | >300 CFU | NG | |
| | 5 | NG | 7 CFU | 1 CFU | >300 CFU | NG | CG | 1 CFU | |
| 0.5 | 60 | 1 CFU | >300 CFU | NG | — | | | | |
| | | 3 CFU | >300 CFU | 3 CFU | | | | | |
| | 30 | >300 CFU | CG | 4 CFU | — | | | | |
| | 15 | 42 CFU | CG | 10 CFU | — | | | | |
| | 5 | 75 CFU | CG | >300 CFU | — | | | | |

Note:
NG—no growth;
CFU—number of colony-forming units in 1 ml;
CG—confluent growth

TABLE 3

Bactericidal activity of zinc methacrylate-acetate

| Concentration, % wt. | Time of exposure, min. | Zinc methacrylate-acetate | | |
|---|---|---|---|---|
| | | E. coli 1257 | S. aureus 906 | P. aeruginosa |
| 5 | 5 | NG | >300 CFU | 1 CFU |
|   |   | NG | >300 CFU | NG |
|   |   | NG | >300 CFU | NG |
| 2.5 | 60 | NG | 1 CFU | NG |
|   |   | NG | 4 CFU | NG |
|   |   | NG | 95 CFU | NG |
|   | 30 | NG | >300 CFU | NG |
|   |   | NG | >300 CFU | 1 CFU |
|   |   | NG | >300 CFU | NG |
|   | 5 | 24 CFU | CG | CG |
|   |   | 113 CFU | CG | CG |
|   |   | 180 CFU | CG | CG |
| 1.0 | 60 | NG | CG | 3 CFU |
|   |   | NG | CG | 93 CFU |
|   |   | NG | CG | 78 CFU |
|   | 30 | NG | CG | >300 CFU |
|   |   | NG | CG | >300 CFU |
|   |   | NG | CG | >300 CFU |
|   | 5 | CG | CG | CG |
|   |   | CG | CG | CG |
|   |   | CG | CG | CG |

Note:
NG—no growth;
CFU—number of colony-forming units in 1 ml;
CG—confluent growth

TABLE 4

Fungicidal activity of the proposed salts

| Example No. | Test material | Additive Name | Content, % wt. | Tolerance time, days |
|---|---|---|---|---|
| 11 | Polyvinyl chloride emulsion | Zinc methacrylate-salicylate | 0.5 | 16 |
| 12 | Polyvinyl chloride emulsion | Zinc methacrylate-sulfosalicylate | 0.5 | 16 |
| 13 | Polyvinyl chloride emulsion | Zinc acrylate-benzoate | 0.5 | 11 |
| 14 | Polyvinyl chloride emulsion | Copper methacrylate-benzoate | 0.5 | 17 |
| 15 (compar.) | Polyvinyl chloride emulsion | ZMA | 5 | 22 |
| 16 (compar.) | Polyvinyl chloride emulsion | — | — | 6 |
| 17 | Paper impregnated with latex SKS 65 GP | Zinc methaerylate-salicylate | 0.5 | 8 |
| 18 | Paper impregnated with latex SKS 65 GP | Zinc methacrylate-sulfosalicylate | 0.5 | 16 |
| 19 (compar.) | Paper impregnated with latex SKS 65 GP | ZMA | 0.5 | 12 |
| 20 (compar.) | Paper impregnated with latex SKS 65 GP | — | — | 4 |
| 21 | Paper impregnated with petrolatum base | Zinc methacrylate-sulfosalicylate | 4.7 | 20 |
| 22 (compar.) | Paper impregnated with petrolatum base | ZMA | 4.7 | 16 |
| 23 (compar.) | Paper impregnated with petrolatum base | — | — | 15 |

What is claimed is:

1. A biocide comprised of a zinc or copper (II) salt having a general formula:

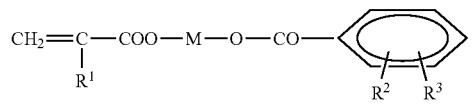

wherein M is Zn or Cu, $R^1$ is selected from the group consisting of hydrogen and methyl;

$R^2$ is selected from the group consisting of hydrogen and OH;

$R^3$ is selected from the group consisting of $C_1$-$C_3$ alkyl and a $SO_2OH$ group.

2. A method of using the biocide according to claim 1 as a bactericide, the method comprising dissolving said biocide in an aqueous medium to form a solution having a concentration in a range from 0.5% to 2%, and treating an object with the solution.

3. A method of using the biocide according to claim 1 as a fungicide, the method comprising treating a material to be preserved from fungi or spores of fungi with said biocide.

* * * * *